US010974021B2

(12) United States Patent
Walzman

(10) Patent No.: US 10,974,021 B2
(45) Date of Patent: Apr. 13, 2021

(54) DUAL LUMEN MICROCATHETER

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 120 days.

(21) Appl. No.: 15/731,810

(22) Filed: Aug. 3, 2017

(65) Prior Publication Data

US 2018/0104443 A1 Apr. 19, 2018

Related U.S. Application Data

(60) Provisional application No. 62/496,506, filed on Oct. 19, 2016.

(51) Int. Cl.
*A61M 25/00* (2006.01)
*A61B 17/34* (2006.01)
*A61B 17/12* (2006.01)
*A61M 25/10* (2013.01)

(52) U.S. Cl.
CPC ... *A61M 25/0015* (2013.01); *A61B 17/12022* (2013.01); *A61B 17/12186* (2013.01); *A61B 17/3415* (2013.01); *A61M 25/003* (2013.01); *A61M 25/008* (2013.01); *A61B 17/12113* (2013.01); *A61B 17/12159* (2013.01); *A61B 17/3417* (2013.01); *A61B 2017/1205* (2013.01); *A61M 25/10* (2013.01); *A61M 2025/0042* (2013.01)

(58) Field of Classification Search
CPC .. A61M 25/10; A61M 25/0026; A61M 25/06; A61M 25/0067; A61M 25/0023; A61M 25/0071; A61M 25/0662; A61M 2025/0042; A61M 2210/0693; A61M 25/0125; A61M 25/104; A61F 2/013
See application file for complete search history.

(56) References Cited

U.S. PATENT DOCUMENTS

| | | |
|---|---|---|
| 4,755,176 A | 7/1988 | Patel |
| 4,784,638 A | 11/1988 | Ghajar et al. |
| 4,970,926 A | 11/1990 | Ghajar et al. |
| 5,180,387 A | 1/1993 | Ghajar et al. |
| 5,380,276 A * | 1/1995 | Miller .............. A61M 1/285 |
| | | 604/264 |
| 5,800,407 A * | 9/1998 | Eldor .............. A61M 25/007 |
| | | 604/264 |
| 5,954,687 A | 9/1999 | Baudino |
| 6,223,637 B1 | 5/2001 | Hansen |
| 6,569,145 B1 | 5/2003 | Shmulewitz |
| 8,403,911 B2 | 3/2013 | Adams et al. |
| 8,496,629 B2 | 7/2013 | McKinnon et al. |
| 9,364,634 B2 | 6/2016 | Adams et al. |
| 9,399,112 B2 | 7/2016 | Shevgoor et al. |

(Continued)

*Primary Examiner* — Brandy S Lee
*Assistant Examiner* — Nidah M Hussain

(57) ABSTRACT

The present disclosure relates to the field of endovascular treatment. More particularly, the present invention is a tool designed to implement an endovascular treatment by the implementation of two or more lumens on a microcatheter and/or having a side hole in a single lumen. The present invention ameliorates the medical difficulty associated with making a good plug to prevent reflux of liquid embolic along catheter and maximize distal penetration, usually in treatment of arteriovenous malformations (AVM) and arteriovenous fistulas (AVF).

15 Claims, 3 Drawing Sheets

(56) References Cited

U.S. PATENT DOCUMENTS

| | | |
|---|---|---|
| 9,440,043 B2 | 9/2016 | Arora et al. |
| 2007/0073271 A1 | 3/2007 | Brucker |
| 2008/0183128 A1 | 7/2008 | Morriss |
| 2010/0049165 A1* | 2/2010 | Sutherland ........ A61M 25/0069 604/508 |
| 2013/0310687 A1* | 11/2013 | Takizawa ............ A61M 25/104 600/435 |
| 2014/0039459 A1* | 2/2014 | Folk ................. A61B 17/12186 604/509 |
| 2015/0088100 A1* | 3/2015 | Oborn ................... A61M 25/02 604/523 |
| 2015/0174381 A1* | 6/2015 | Morita ............... A61M 25/0082 604/513 |
| 2018/0104443 A1* | 4/2018 | Walzman .......... A61M 25/0015 |
| 2019/0001113 A1 | 1/2019 | Call |

\* cited by examiner

DUAL LUMEN MICROCATHETER

FIELD OF THE INVENTION

The present disclosure relates to the field of endovascular treatment. More particularly, the present invention is a tool designed to implement an endovascular treatment.

BACKGROUND OF THE INVENTION

Prior Art

The present invention is a tool to safely and effectively implement an endovascular treatment. In medicine, a catheter is a thin tube serving a broad range of functions. Catheters are medical devices that can be inserted in the body to treat diseases or perform a surgical procedure.

Catheters can be inserted into a body cavity, duet, or vessel. Functionally, they allow drainage, administration of fluids or gases, access by surgical instruments, and also perform a wide variety of other tasks depending on the type of catheter.

A double lumen catheter is a long, flexible medical device that consists of one hollow tube within another hollow tube and/or two hollow tubes fused together side-by-side. The word "lumen means an open area inside an object, as in the lumen of the intestine. It differs from a single lumen catheter in that it enables two different actions to take place close together and with less tissue trauma. These actions could be the withdrawal of fluid or the insertion of fluid, air or small medical devices. These catheters can be used to drain blood, urine or unwanted liquid, such as from the lungs or abscesses.

A double lumen catheter can be made from one of many flexible materials, such as silicone, latex, Teflon® or polyurethane. The catheter might have a syringe associated with it that can be removed after the catheter is in place and access points—called hubs or injection ports—on the ends of the lumens that remain outside the body. Often, the two lumens in the catheter open in different places. Sometimes, they will open on opposite sides of the body of the tube, and other times, one will open at the tip of the tube and the other will open a short distance away from the tip or immediately side by side.

A microcatheter is a single-lumen device that can be loaded on a guide wire in order to place it in or near a target area. The microcatheters are sometimes used to help the physician to cross a lesion, prior to balloon dilatation and stenting. They can be used to give mechanical support to the guide wire, enhancing its ability to transmit force to a device at the end of the guide wire. occlusion. They can also serve to deliver coils and/or liquid embolics to a target lesion.

Some microcatheters use a coaxial tube which is designed to increase procedural efficiency and reduce the risks of procedural problems, such as kinking. A typical coaxial system includes a 0.021 Glidewire GT and incorporates an attached hub, which allows the wire to be preassembled and fixed via a Luer-lock assembly onto a Terumo Progreat microcatheter. The combination allows the guide wire and microcatheter to be flushed simultaneously while still in the packaged hoop and it enhances the clinician's ability to negotiate the vasculature and reach the targeted vessel.

One use of microcatheters, such as used by Marathon and Appolo (Medtronic) is for delivery of liquid embolics such as Onyx (Medtronic), Squid, Balt (not available in U.S. at this time), Phil, (Microvention FDA approved) or BCA and others, to a target lesion. A well described technique to optimize Onyx delivery into a brain arteriovenous malformation is the "plug and push" technique.

Using the "plug and push" technique, a plug of Onyx is formed around the treatment catheter prior to injecting Onyx into the AVM (Arteriovenous Malformation). The plug mitigates the risk of backflow and possible injection of Onyx into a normal branch, while facilitating deeper Onyx penetration into the target lesion.

Prior art also reports that in select cases a Scepter balloon can be used with Onyx, and the balloon can be inflated and the balloon substitutes for the plug. Another potential use of the present invention is to more safely and effectively deliver coils into a "wide-necked" aneurysm. Balloon assisted coiling, stent assisted coiling, and dual microcatheter techniques have also been described for this application.

Existing microcatheter technology is not able to ameliorate the medical difficulties associated with reflux of too much liquid embolic during plugging when injecting certain liquid embolics. Additionally, using existing art results in spending a long time trying to inject tiny amounts of liquid embolics to try and create an adequate "plug". It also results in a lot of radiation exposure to the patient and staff, high amounts of anesthesia time and high failure rates while trying to make a plug.

The current art such as balloon assisted coiling has higher embolic risk, dual microcatheter techniques also has that, and takes up more room in vessels and in guide catheters—so can preclude adjunctive use of a balloon, and requires two separate aneurysm catheterizations—with risks of complications like aneurysm rupture. Stent assisted techniques require the patients to be loaded on aspirin and Plavix—many patients cannot have these drugs, especially in the setting of a ruptured aneurysm.

While dual lumen catheters are taught by the prior art, such as Miller (U.S. Pat. No. 5,683,640), they are not capable of endovascular activity. More specifically, the dual lumen catheters are taught by the prior art are not capable of the generation and placement of proximal plugs.

Advantages of the Current Invention

The present invention substantially fulfills the forgoing unmet needs. The present invention contains one or more lumen microcatheter and side hole microcatheter. Also in some versions, the present invention is equipped with a "detachable tip" to allow creation of a more dense plug without risk of gluing in the catheter.

The present invention would enable practitioner to have the ability to easily make a proximal Onyx 34 (or similar) plug through the lumen with the more proximal of the 2 distal holes. Once the plug is made, Onyx 18 (or similar) could easily be infused through the distal ending lumen. This would make the "plug and push" technique easily accessible to all practitioners, and more effective for all as well. Currently. the "plug and push" technique is somewhat of an art. There is a fairly steep learning curve, and many practitioners never really master it. Furthermore, even in the best hands, sometimes there is too much reflux during plug formation and additional injection for distal penetration (the "push") has to be aborted, lest further reflux occlude any normal branches, which in intracranial vessels can lead to a stroke.

The version of the present invention with a detachable tip to the dual lumen microcatheter would have several significant advantages over currently available technologies. First, the ability to easily and consistently make a proximal plug in all cases. Second, if you use N-Butyl Cyanoacrylate (tissue adhesive) or an equivalent for the proximal plug, this would make for more reliable detachment in all cases, avoiding the increased risk associated with vessel torsion during pull-out in the 70%+ of cases Apollo and similar catheters currently fails to detach. A need exists to control flow during initial injections to prevent distal emboli.

The prior art teaches the use of stopping and reversing blood flow, but not in the way taught by the present invention.

Thus at present, there does not appear to be a device that allows for reliable plug formation when injecting liquid embolic. The disclosed invention addresses this unmet need.

BRIEF DESCRIPTION OF THE DRAWINGS

The invention will be better understood and objects other than those set forth above will become apparent when consideration is given to the following detail description thereof Such description makes reference to the annexed drawings wherein:

FIG. 1. shows Luer-lock (15) on each proximal lumen hole (14), (16) and (18); FIG. 1 also depicts secondary proximal lumen, also known as proximal side hole lumen (16) and balloon lumen (18); and still further depicts catheter (11) with a balloon (20), detachment site (13) and distal hole of secondary lumen (17).

DETAILED DESCRIPTION OF THE INVENTION

Figure 1:
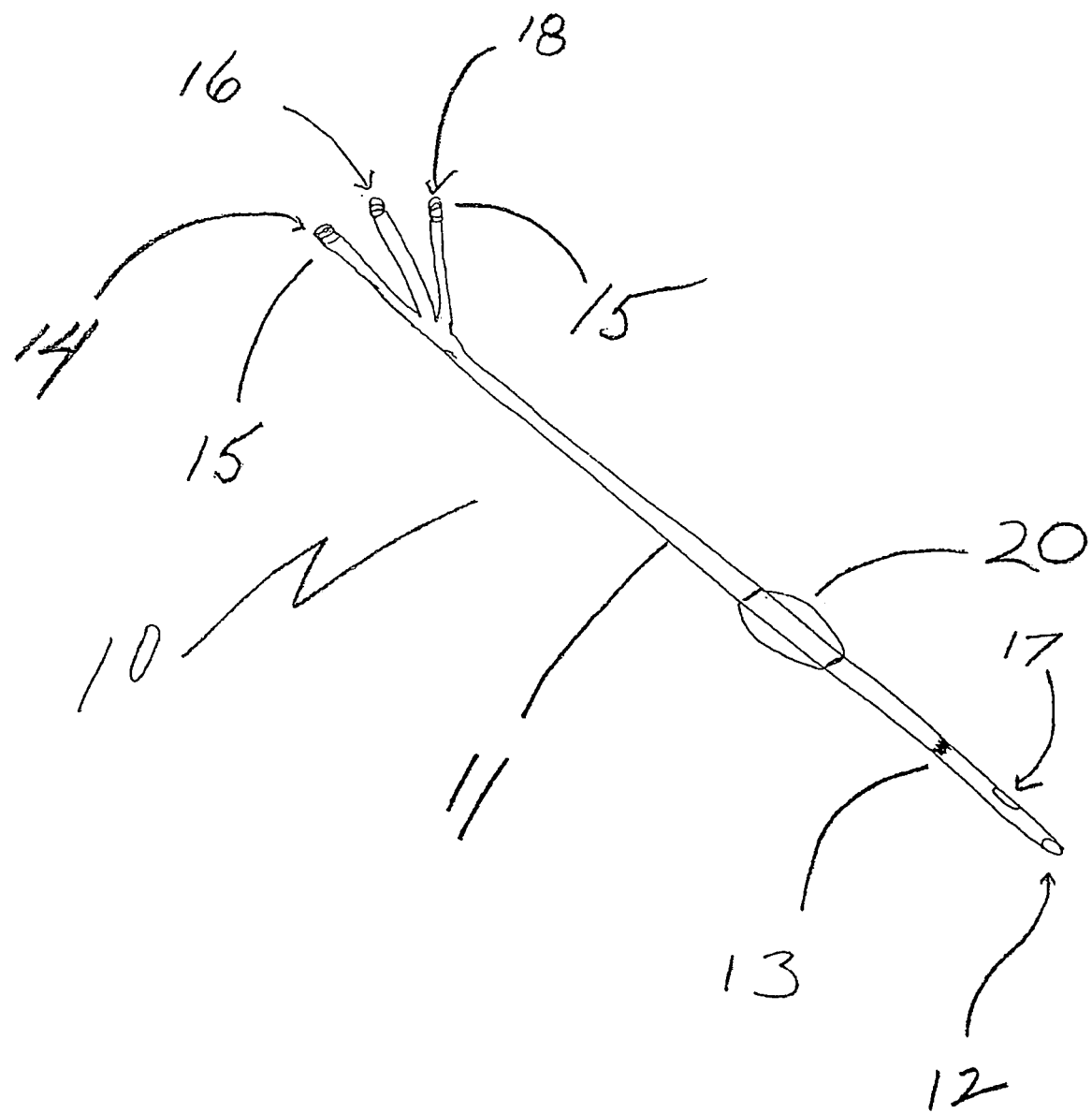
FIG. 1. depicts dual lumen microcatheter (10) with primary distal hole (12) and primary proximate hole (14).
Figure 2:
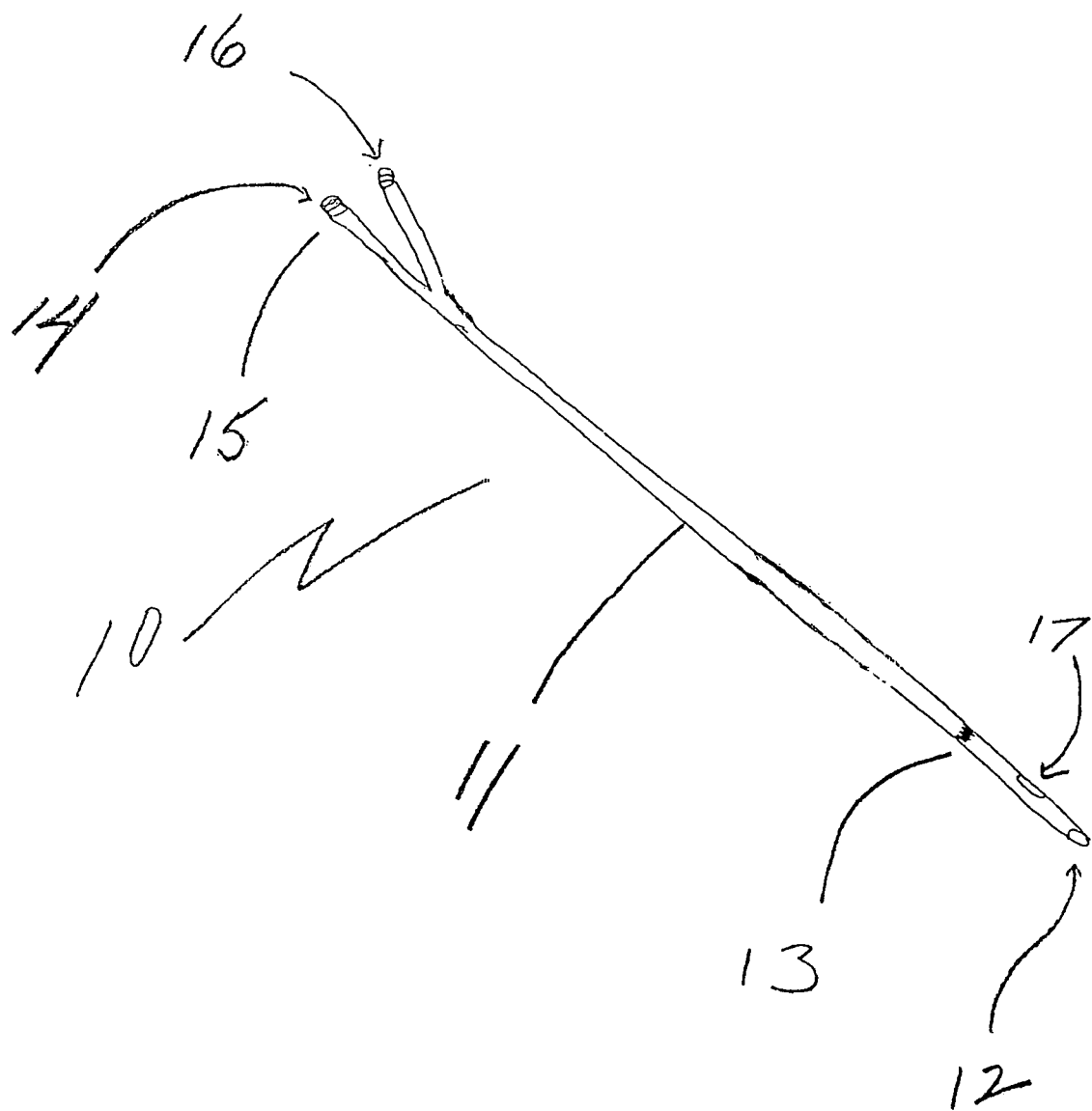
FIG. 2 depicts a microcatheter equivalent to that shown in FIG. 1 without the embedded balloon and its associated balloon; the embodiment shown in FIG. 2 is ideally dimensioned to fit within the intermediate catheter of FIG. 3, and hence pass through FIG. 3 (or be used independently).
Figure 3:
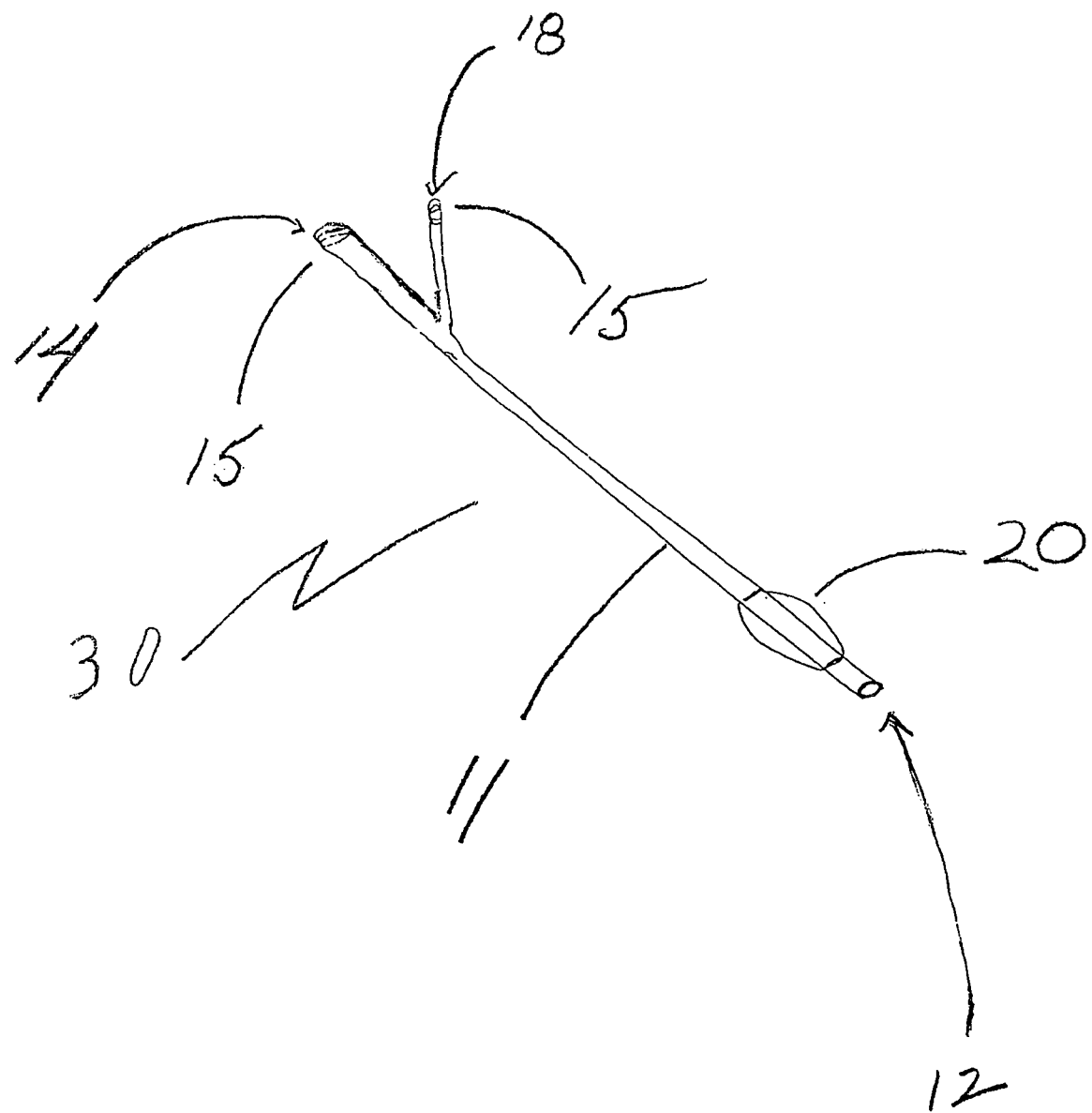
FIG. 3 depicts a dual lumen microcatheter (30) with an intermediate intracranial or intracranial "guide" catheter with an inner diameter of approximately 0.8 mm to 3 mm (or 9 French); this embodiment a sufficiently large inner diameter between access holes (12) and (14) so as to allow insertion of the embodiments shown in FIG. 2 to pass there through. The present invention is scalable for application in peripheral vascular and cardiac uses.

The present disclosure teaches a microcatheter with two separate lumens. The lumen that ends more proximally might end/exit perhaps 0.2 mm to 6 cm (sweet spot 5 mm-30 mm) more proximal than the other lumen. Other length differences are possible as well—one version can be used for "dual microcatheter" technique to coil aneurysms—in this version two lumens might end 0 mm to 15 mm apart. The microcatheter of the current invention comprises at least two lumens fused onto a proximal end, a primary distal hole and a secondary distal hole at the distal end of said catheter. The concept is otherwise primarily for the delivery of liquid embolics.

In order to make the formation of the proximal plug even easier and more controlled, a balloon can be added more proximally on the catheter, or on a separate distal access catheter (DAC also known as the intermediate catheter), in order to temporarily arrest flow of blood while forming the plug with Onyx or Glue. This balloon could be on the dual lumen microcatheter itself. Alternatively, to avoid affecting the deliverability of the microcatheter, there can be a separate balloon mounted intermediate catheter, through which the dual lumen microcatheter can be delivered; and the balloon on the intermediate catheter can then be used to temporarily stop flow during the "plug" formation.

The present invention can have both detachable and non-detachable tips. Side hole(s) might also be slits in either direction, and/or multiple holes along the same region of the distal catheter. It can have or not have a balloon proximally attached.

All versions of the present invention would have radio opaque markers at the distal end (with the distal hole), at the end of the other lumen/the side hole or in the single lumen versions at the site of the side hole(s)/slit(s), and for versions with a balloon at the proximal end of the balloon and at the distal end of the balloon.

The present invention when used to arrest flow is most useful for injecting liquid embolics for arteriovenous malformation fistula treatment and related procedures. The present invention when used to reverse flow is most useful for injecting liquid embolics for liquid embolics for arteriovenous malformation and arteriovenous fistula or stroke.

The present invention is used to inject glue or plugging material using a balloon mounted removable catheter. More particularly, the present invention arrests flow for side-injection of glue and proximal control during treatment. The present invention is used to arrest or reverse flow of blood during thrombectomy to facilitate clot retrieval and minimize instances of distal emboli.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. An intravascular, multiple lumen catheter adapted to deliver first and second liquid embolics, the catheter comprising at least a primary proximal end hole and a secondary proximal end hole, a primary distal hole at a distal end of said catheter in communication with a dedicated separate primary lumen in communication with the primary proximal hole, and a secondary distal hole proximal to said distal end of said catheter in communication with a dedicated separate secondary lumen in communication with the secondary proximal hole, and at-least-one detachment site capable of separating a portion of said catheter located between said detachment site and said distal end;

and wherein the secondary distal hole is a side hole in communication with the secondary lumen and configured for exit of the first liquid embolic flowing through the secondary lumen to form a plug around the catheter prior to injection of the second liquid embolic through the primary distal hole, the plug reducing the risk of backflow of the second liquid embolic, and the second liquid embolic is different from the first liquid embolic.

2. The catheter of claim 1, further including a luer-lock disposed at a proximal end of at least one of said at least two dedicated separate lumens at one of at least two proximal end holes.

3. The catheter of claim 1, wherein said secondary distal hole is disposed approximately 10 cm or less proximal to said primary distal hole.

4. The catheter of claim 1, further including a balloon disposed thereon, the balloon disposed proximal of the detachment site and proximal of the side hole, and one additional lumen which serves exclusively to inflate and deflate said balloon, wherein said balloon is in position proximal to said secondary distal hole to arrest flow of the first liquid embolic while forming a plug from the first liquid embolic.

5. The catheter of claim 4, wherein the catheter is enclosed in an intermediate catheter, said intermediate catheter acting as a support catheter for delivery of said catheter therethrough.

6. The catheter of claim 1, wherein the catheter is enclosed in an intermediate catheter, said intermediate catheter acting as a support catheter for delivery of said catheter therethrough, the intermediate catheter having a balloon disposed on said intermediate catheter to arrest flow whole forming the plug from the first liquid embolic.

7. A method of using the catheter of claim 1, comprising the steps of
(a) positioning said distal end of said catheter proximal to a target lesion;
(b) injecting the first liquid embolic through said secondary proximal hole and through said side hole, under fluoroscopic guidance, until an adequate proximal plug is complete around the catheter to reduce backflow into a normal branch;
(c) waiting for said proximal plug to harden;
(d) subsequent to step (b) injecting the second liquid embolic through said primary distal hole, and "pushing" more said second liquid embolic into the target lesion, until desired penetration of said lesion with said second liquid embolic is achieved;
(e) detaching a portion of said catheter at said detachment site; and
(f) removing said portion of said catheter located between said detachment site and said proximal end of said catheter, while leaving said portion of said catheter located between said detachment site and said distal end.

8. The method of using the catheter of claim 7, comprising the steps of
(a) inflating a balloon to arrest flow while forming the plug; and
(b) deflating said balloon.

9. The catheter of claim 1, wherein the detachment site has a diameter not exceeding a diameter of the catheter adjacent the detachment site.

10. The method of using the catheter of claim 1, further comprising the steps of injecting the first liquid embolic through the side hole, waiting for the plug to be made around the catheter and then injecting the second liquid embolic through the primary distal hole.

11. A multiple lumen catheter, adapted to deliver first and second liquid embolics, adapted for intravascular use, comprising:

a primary lumen and a separate secondary lumen;
at least a primary proximal end hole and a secondary proximal end hole,
a primary distal hole at a distal end of said multiple lumen catheter in communication with the primary lumen in communication with the primary proximal hole, and
a secondary distal hole proximal to said distal end of said multiple lumen catheter
wherein the secondary distal hole is a side hole in communication with a separate secondary lumen in communication with the secondary proximal hole, the side hole configured for exit of the first liquid embolic to form the plug around the catheter to reduce the risk of backflow of the second liquid embolic, the first liquid embolic injected before the second liquid embolic, and the first liquid embolic being different than the second liquid embolic,
said multiple lumen catheter being positioned in an intermediate catheter, said intermediate catheter acting as a support catheter for delivery of said multiple lumen catheter therethrough, and a balloon is disposed on said intermediate catheter, and is configured to arrest flow while forming the plug.

12. The multiple lumen catheter of claim 11, wherein an outer wall of the catheter is continuous along a length.

13. The multiple lumen catheter of claim 11, wherein a continuous uninterrupted lumen is defined within a wall of the catheter.

14. The method of using the catheter of claim 11, further comprising the steps of injecting the first liquid embolic through the side hole, waiting for the plug to be made around the catheter and then injecting the second liquid embolic through the distal hole.

15. A method of using the catheter of claim 11, comprising the steps of
(g) positioning said distal end of said catheter proximal to a target lesion;
(h) injecting the first liquid embolic through said secondary proximal hole and through said side hole, under fluoroscopic guidance, until an adequate proximal plug is complete around the catheter to reduce backflow into a normal branch;

(i) waiting for said proximal plug to harden;
(j) subsequent to step (b) injecting the second liquid embolic through said primary distal hole, and "pushing" more said second liquid embolic into the target lesion, until desired penetration of said lesion with said second liquid embolic is achieved;
(k) detaching a portion of said catheter at said-detachment site; and
(l) removing said portion of said catheter located between said detachment site and said proximal end of said catheter, while leaving said portion of said catheter located between said detachment site and said distal end.

\* \* \* \* \*